(12) United States Patent
Iotti et al.

(10) Patent No.: US 10,765,254 B2
(45) Date of Patent: *Sep. 8, 2020

(54) DISPENSING SYSTEM FOR DELIVERING CUSTOMIZED QUANTITIES OF DIETARY AND NUTRACEUTICAL SUPPLEMENTS AND FLAVOR IN A SINGLE AND MULTI-SERVE CONFIGURATIONS

(71) Applicant: Mixfit Inc., Danvers, MA (US)

(72) Inventors: Marco Iotti, Lausanne (CH); Enald Beqiraj, Salem, MA (US); Reza Zanjani, Orlando, FL (US); Jesse Caruso, Danvers, MA (US); Gianluca Colantonio, Grangettes (CH)

(73) Assignee: MIXFIT INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/978,936

(22) Filed: May 14, 2018

(65) Prior Publication Data

US 2020/0000270 A1    Jan. 2, 2020

Related U.S. Application Data

(63) Continuation-in-part of application No. 15/662,422, filed on Jul. 28, 2017.

(51) Int. Cl.
*A47J 31/40* (2006.01)
*A23L 33/00* (2016.01)
(Continued)

(52) U.S. Cl.
CPC ............ *A47J 31/402* (2013.01); *A23L 33/00* (2016.08); *A47J 31/407* (2013.01); *A47J 31/461* (2018.08);
(Continued)

(58) Field of Classification Search
USPC .................................................. 700/231–244
See application file for complete search history.

(56) References Cited

U.S. PATENT DOCUMENTS 8,490,829 B2    7/2013   Deo et al.

FOREIGN PATENT DOCUMENTS

| WO | 2011008950 A2 | 1/2011 |
| WO | 2016109018 A1 | 7/2016 |

OTHER PUBLICATIONS

International Search Report for International Application No. PCT/US2018/043682; International Filing Date: Jul. 25, 2018; dated Nov. 30, 2018; 7 pages.

(Continued)

*Primary Examiner* — Timothy R Waggoner
(74) *Attorney, Agent, or Firm* — Muncy, Geissler, Olds & Lowe, P.C.

(57) ABSTRACT

A system and method for delivery of a beverage with a customized quantities of dietary and nutraceutical supplements in real time having a beverage delivery apparatus with a plurality of storage compartments. Each of the storage compartments configured to contain at least one seed capsule that contains the dietary and nutraceutical supplements. The dispensing apparatus for delivering a beverage with customized quantities of dietary and nutraceutical supplements and flavor in single and/or multi-serve configurations is also provided. The system further has a cloud-based data center with a nutrient recommendation engine configured to create a personalized nutrient mix regimen profile and to provide specific recommendation to a user.

11 Claims, 11 Drawing Sheets

(51) Int. Cl.
*G16H 20/60* (2018.01)
*G16H 20/13* (2018.01)
*A47J 31/46* (2006.01)
*A61K 9/00* (2006.01)

(52) U.S. Cl.
CPC ........... *A61K 9/0095* (2013.01); *G16H 20/13* (2018.01); *G16H 20/60* (2018.01)

(56) References Cited

OTHER PUBLICATIONS

Written Opinion of the International Searching Authority for International Application No. PCT/US2018/043682 filed on Jul. 25, 2018; dated Nov. 30, 2018; 9 pages.

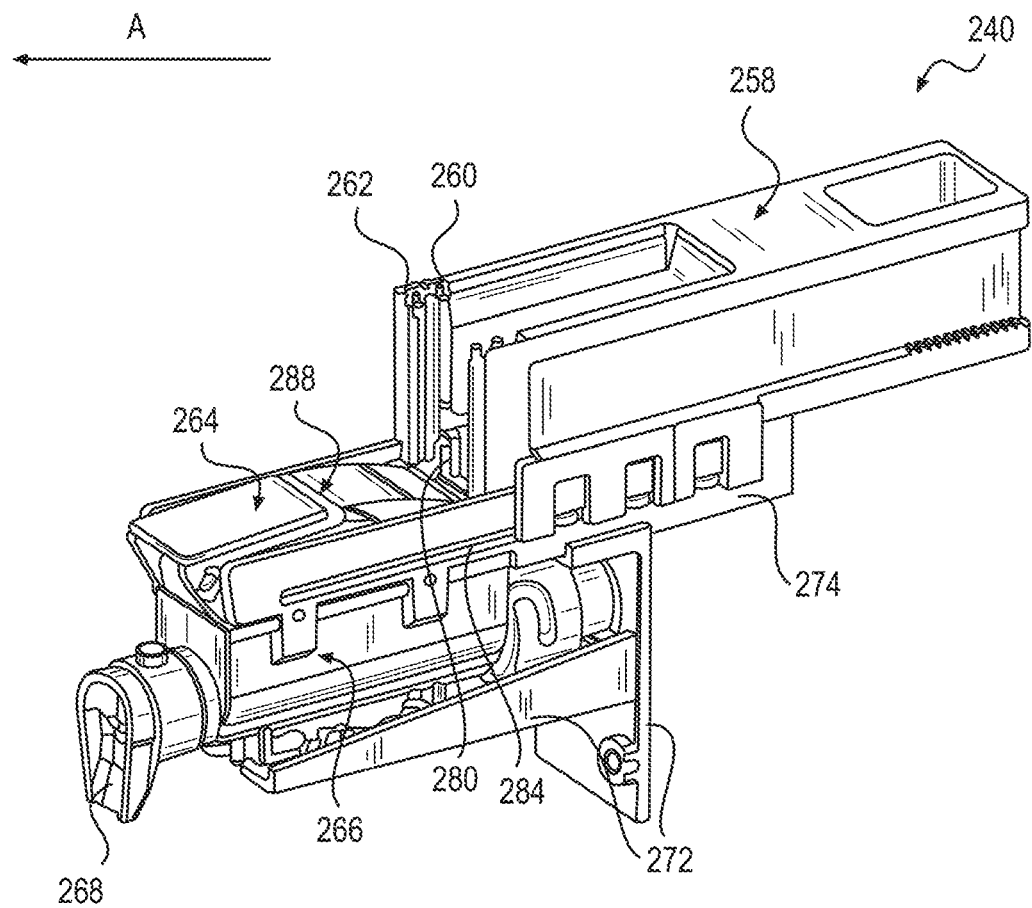
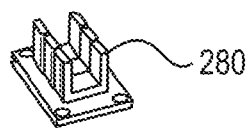
FIG. 7

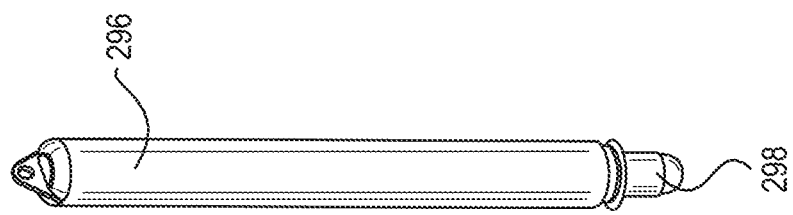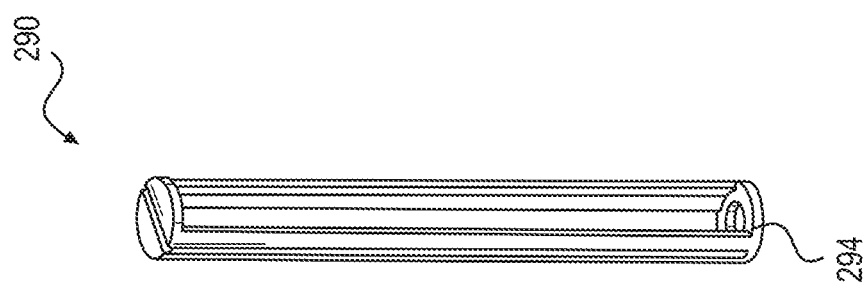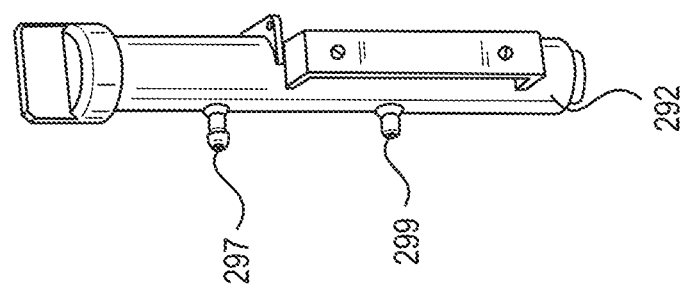
FIG. 9

DISPENSING SYSTEM FOR DELIVERING CUSTOMIZED QUANTITIES OF DIETARY AND NUTRACEUTICAL SUPPLEMENTS AND FLAVOR IN A SINGLE AND MULTI-SERVE CONFIGURATIONS

CROSS REFERENCE TO RELATED APPLICATIONS

This application is a continuation-in-part of U.S. application Ser. No. 15/662,422, filed on Jul. 28, 2017; the entire content of which is hereby incorporated by reference.

BACKGROUND OF THE INVENTION

Field of the Invention

The present invention relates to customized dietary product dispensing systems and, more particularly, to a dispensing system for delivering customized quantities of dietary and nutraceutical supplements, and to a method of using the dispensing system.

Description of the Background Art

Healthcare is undergoing a technological transformation, and it is imperative for the industry to leverage new technologies to collect, track, and transform consumer digital health data into meaningful and actionable insight to create engagement. The need for consumer engagement in the healthcare industry has never been higher. A catalyst is needed to bridge the divide in digital health, and that catalyst is dietary supplements.

Today, there are more than 200 million Americans who regularly consume dietary supplements. However, these supplements lack personalization, and their "one-size-fits-all" approach causes many consumers to fail to achieve the desired health benefits by either taking the ineffective dosage, or simply supplements that do not achieve the desired effects and/or results.

To understand what products will be most beneficial and how to address the specific health issues, many consumers have turned to the Internet.

Through the Internet, individuals may seek out health and nutrition information to educate themselves about a healthier personal lifestyle and use this detailed information to make informed purchase decisions. However, even with the availability of this information through the Internet, it is very difficult for individual consumers to navigate through the myriad of health studies and decide what they should and should not consume. Furthermore, many consumers dismiss such important health information and resort to consuming eight, twelve, or even eighteen pills a day just to ensure that they are receiving sufficient amounts of vitamins, minerals, and anti-oxidants from generalized formula supplements made for the average person.

Unfortunately, taking these generalized formula supplements made for the average person means ingesting binders, excessive fillers, and lubricants, as well as micronutrients in each menu of pills. These various pills are often difficult to locate for purchase, are hard to swallow and may contain some vitamins or minerals that are not needed or may not have enough of what is in fact needed. In turn, this leads many individuals to give up on their personal supplement program before the two or three months it takes for such programs to realize their full health potential.

Moreover, there is no readily accessible or reliable way for consumers to measure the effectiveness of their dietary supplements. Without knowing if their supplements are having the intended effects, millions of people are habitually consuming the same supplements without knowing whether taking the supplements have any effect on their health and/or fitness goals.

Monitoring the nutrients contained in the consumed nutrition and/or supplements is often considered difficult or laborious. In some cases, it may also be difficult for people to monitor the nutrient contents in the consumed food and/or drink or other substances contained in foods, and medicaments, which may, for example, cause illnesses or make allergies worse. For example, people may have difficulties in remembering or generally in knowing all nutrients harmful for them, in which case, for example when shopping, it may be difficult for a person to know the suitability of a certain product for him or her. Especially, if one thinks of the overall effect of nutrients acquired in one day or even one week, it is almost impossible to find out the suitability, goodness and/or effect of a certain foodstuff in relation to the overall effect of nutrients obtained in one day or one week.

On the other hand, dietary supplement and food manufacturers are spending billions of dollars every year on research and development, product testing, and acquiring data to improve their products and increase sales. However, despite their exorbitant spending, there is no reliable method for collecting post-market product usage data after the initial point of sale of the products. More importantly, it is essentially impossible to obtain real-world effectiveness data of dietary supplements and food products on a large scale. In other words, the nutrient supplement and food brands are not able to determine if their products are having the intended effects on their customers.

In addition, the healthcare system has been focused on responding to already occurring health events like illness, chronic condition onset, and injury. In more recent times, however, this reactive model of health care has been mitigated by putting more emphasis on illness and injury prevention.

The focus on prevention has been directed toward medical screening for early detection of illness and on identification of individuals who may be at-risk for a particular condition, based on an assessment of risk factors/predisposition to certain illnesses, such as genetic screening, or in alternative, life style choices, such as nutrition intake and level of physical activity. The acquired parameters can be transmitted to a processing unit for subsequent analysis, with feedback being provided to a healthcare provider or consumer to allow for early detection of an illness.

Moreover, lifestyle choices like nutrition, physical activity and fitness play a significant role in the overall health and wellness of an individual. For a number of chronic conditions such as diabetes, the ability to adhere to recommended lifestyles choices in terms of nutrition and physical fitness plays a significant role in maintaining the quality of life and keeping the chronic conditions under control. Currently, however, consumers do not have many resources that allow them to manage the aspects of their health and wellness outside of clinical environments, including nutrition, fitness/physical activity levels, as well as in home medical and vitals measurement (i.e., measurement of physiological parameters).

Therefore, a need exists for a system and method that integrates into a easy to use and understand personalized health and wellness management system that is capable of capturing and tracking health and wellness data, which encompasses each of physiological data, nutritional data, and physical activity data for a consumer. A need also exists for a digitally customizable dispensing system for dietary and nutraceutical supplements to be dispensed to a consumer based on the real-time health and wellness data.

Even further, for many years publications and supermarket checkout stands listed approximate calorie/fat/sodium, and other content of generic, and sometimes brand-name items. These counts were used to monitor diet and required the consumers to look up the food item, estimate serving size and determine the nutritional values found for the food item or nutrition supplement. The FDA now requires labeling of food and nutritional products with specific nutrition facts. This allowed the consumer to gain a more precise estimation of nutrition intake by using nutrition values determined specifically for the products in question.

It is, therefore, an object of this invention to disclose a digitally customizable dispensing system for dietary and nutraceutical supplements that autonomously elects, adjusts, recommends and dispenses customized nutrients based on scientifically and digitally validated modular algorithm contingent upon consumer's real-time digitally-generated health and wellness data, and a method of using such dispensing system.

SUMMARY OF THE INVENTION

The present invention discloses a system for delivering customized quantities of dietary and nutraceutical supplements to a user having a beverage delivery apparatus and a nutrient recommendation engine for determining nutrition recommendation parameters of the dietary and nutraceuticals supplements that are required to achieve a user's predetermined goals.

According to an embodiment of the present disclosure the beverage delivery apparatus comprises a plurality of storage compartments. Each of the storage compartments configured to receive at least one canister that contains the dietary and nutraceutical supplements. The beverage delivery apparatus further includes a receiving chamber that is configured to receive the dietary and/or nutraceutical supplements from the canister. The receiving chamber allows for an access to a liquid that facilitates blending the dietary and nutraceutical supplements with the liquid to make a customized consumable beverage that contains the specific formulation of dietary and nutraceutical supplements supplied by the canisters.

Adjacent to the beverage delivery apparatus or, in alternative, a part of the beverage delivery apparatus may also have a container configured to provide the liquid into the receiving chamber.

In another embodiment of the present disclosure, a dispensing apparatus for delivering a beverage with customized quantities of dietary and nutraceutical supplements and flavor in single and/or multi-serve configurations is provided. The apparatus comprises a plurality of dispensing units configured to deliver a mixture of the dietary and nutraceutical supplements. In addition, the apparatus includes a single-serve assembly configured to dispense a single serving of the dietary and nutraceutical supplements into the beverage. At least one flavoring component configured to deliver a flavored ingredient to the beverage is also provided. The apparatus may further include a liquid container and a cup.

In an embodiment of the present disclosure, the user data comprises gender, age, weight, height genetic data, bioenergy and nutrients consumption, bioenergy and nutrients intake, and other health data. The user data may also include levels of physical activity and physical fitness data. Moreover, at least some user data is collected in real-time by a monitoring device connected to a cloud-based data center with at least one computer program. Additionally, some of the user data may be provided directly by the user input via a monitoring and/or diagnostic device or a user interface of the beverage delivery apparatus.

The nutrition recommendation parameters of the dietary and nutraceuticals supplements are based on the user data and preset and/or predetermined user's goals and parameters, and determined by the nutrient recommendation engine and communicated to a controller of the dispensing system. Upon the user's confirmation, the beverage delivery apparatus then dispenses customized quantities of dietary and nutraceutical supplements in the customized consumable beverage.

The nutrient recommendation engine may comprise a set of executable instructions such as in the form of software, routines, programs, algorithms, code, logic and the like, which would, for example, facilitate the determination of the customized consumable beverage that contains the specific formulation of dietary and nutraceutical supplements.

In an embodiment of the present disclosure, the cloud-based data center is connected to one or more monitoring device that generates the user data and communicates the user data to the cloud-based data center. The user data is also generated by the user input through, for example, the monitoring device, mobile device or a user interface of the beverage delivery apparatus.

The cloud-based data center further comprises the nutrient recommendation engine configured to create a personalized nutrient mix regimen profile and to provide specific recommendation of a mix of dietary and/or nutraceutical supplements based on the personalized nutrient mix regimen profile of the user and the user data, some of which is collected and transmitted to the cloud-based data center in real-time. The user data comprises information on profiling, biometrics data, direct and indirect input on food consumption, nutritional goals and activities.

In an embodiment of the present disclosure, in order to calculate the precise quantity of nutrients the user's body requires to achieve the user's goals (e.g. preset parameters), the nutrient recommendation engine may utilize the Nutrient Balance Concept (NBC). In addition, In another embodiment of the present disclosure, a modified NBC, Mixfit Balance Concept (MBC) may be used in order to calculate the precise quantity of nutrients. NBC score is modified by integrating specific energy (Kcal) and nutrients (mg) derived from onboarding process or other means from the user such as wearable devices.

The cloud-based data center is also configured to receive automatic real-time updates of the user data from at least one monitoring device, communicate the updated user data to the nutrient recommendation engine, and determine the specific updated recommendation for the personalized mix of the dietary and nutraceutical supplements, which is then dispensed by dispensing apparatus upon the user's confirmation.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 7: is an illustration of an exemplary embodiment of a dispensing unit of the combination beverage delivery apparatus according to the present disclosure;

FIG. 9: is an illustration of an exemplary embodiment of a flavoring component of the combination beverage delivery apparatus according to the present disclosure.

DETAILED DESCRIPTION

Figure 1:
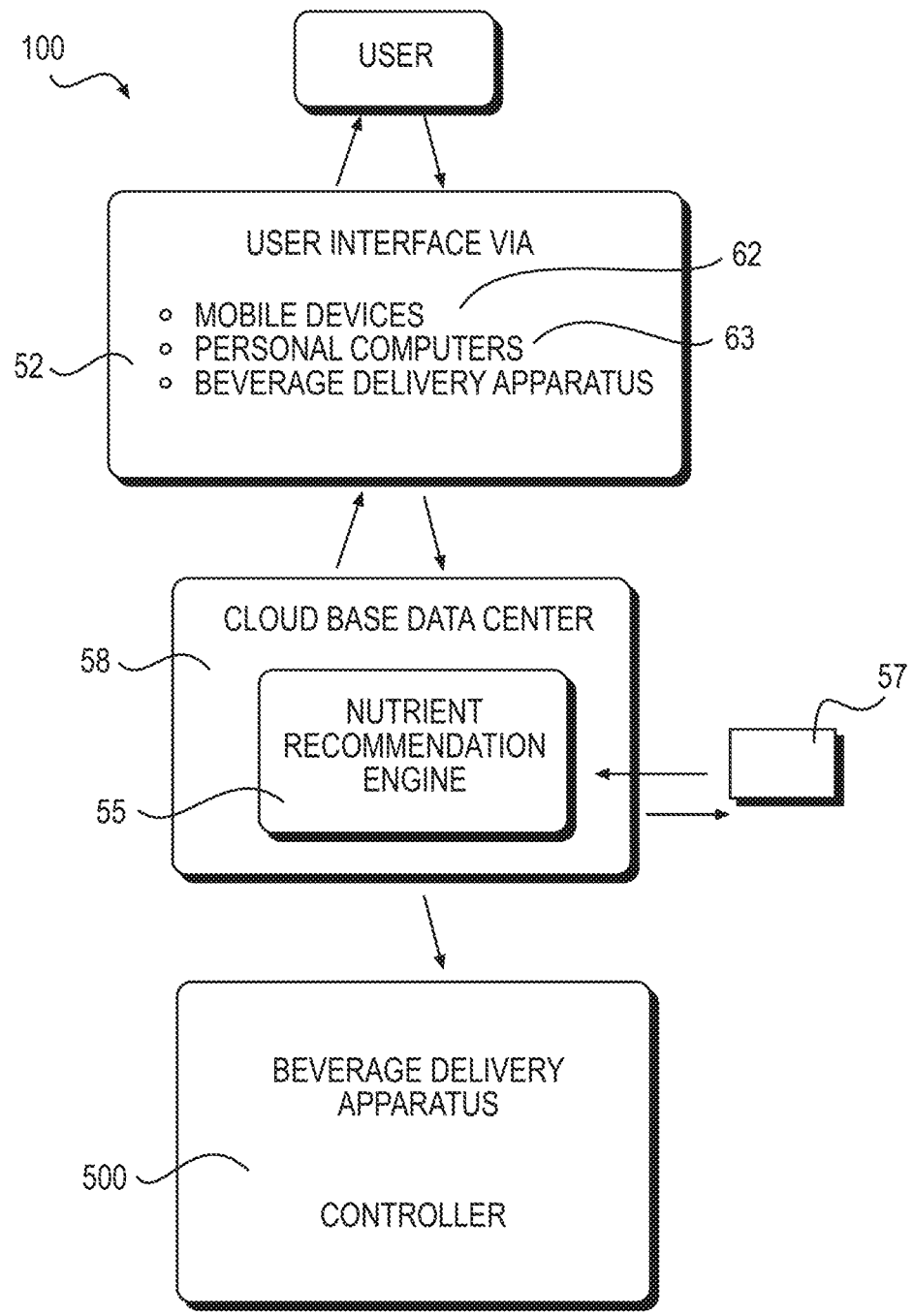
FIG. 1: is a schematic illustration of an exemplary embodiment of a system for delivering customized quantities of dietary and nutraceutical supplements to a user according to the present disclosure.

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "nutraceutical" is a term that is used to describe any product derived from food sources with extra health benefits in addition to the basic nutritional value found in foods. Such products may prevent chronic diseases, improve health, delay the aging process, increase life expectancy, or support the structure or function of the body.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

The present invention is directed to a system 100 for delivering of customized quantities of dietary and nutraceutical supplements to a user. One aspect of the present disclosure, schematically depicted in FIG. 1, can be understood from the system 100 for delivering of customized quantities of the dietary and nutraceutical supplements to the user, comprising: a cloud-base data center 58, a nutrient recommendation engine 55 that communicates with the user interface 52, and a beverage delivery apparatus 10. The beverage delivery apparatus 10 further includes a user interface 52.

In another embodiment of the present invention, the system 100 further comprises a user identification component 57 in communication with the nutrient recommendation engine 55 and the cloud-base data center 58.

In an embodiment of the present disclosure, the user identification component 57 is use of a personal profile every time the user interacts with the system 100. During the onboarding process the user creates his or her own profile through the user interface 52 or another device that is submitted to the cloud-based data center 58 by the user, providing information on profiling, biometrics data, nutritional goals, activities and the like. All subsequent interactions by the user with the system 100 trigger the user identification throughout his/her unique profile.

In an embodiment of the present disclosure, the nutrient recommendation engine 55 is hosted on the beverage delivery apparatus 10. Alternatively, the nutrient recommendation engine 55 is hosted remotely on the cloud-base data center 58.

The nutrient recommendation engine 55 configured to create a personalized nutrient mix regimen profile and to provide specific recommendation of a mix of dietary and/or nutraceutical supplements based on the personalized nutrient mix regimen profile of the user and the user data, some of which is collected and transmitted to the cloud-based data center in real-time.

The user data comprises information on profiling, biometrics data, direct and indirect input on food consumption, nutritional goals and activities.

The cloud-base data center 58 may contain data of the dietary and nutraceutical supplements, the user identification, the user data, user preferences, and the like.

The beverage delivery apparatus according to this disclosure also includes a controller 500 that is configured to receive commands from, for example, the nutrient recommendation engine 55, and to communicate with, for example, a dispensing units of the beverage delivery apparatus. The controller may be configured to compare the user data received from the data center 58 with parameters provided by the nutrient recommendation engine or preset by the user.

In an embodiment of the present disclosure, the controller 500 may be implemented as a processor, microprocessor, digital signal processor or any other logic circuit or combination of circuits providing control connections. The controller 500 is the link between the data center 58 and a software application, for example, the user interface 52 or a mobile application on the user's wireless device, e.g., mobile phone, tablet, or personal computer). Each time the new user data becomes available, the parameters of the recommendation, time of recommendation, nutrient ingredient, amount, coupling factors are affected. This is determined by the modular algorithm powering the nutrient recommendation engine 55. The algorithm can account for 200+ data points. 1 or all data points can affect the recommendation. The user can accept, decline or substitute the nutrients recommended.

Figure 2:
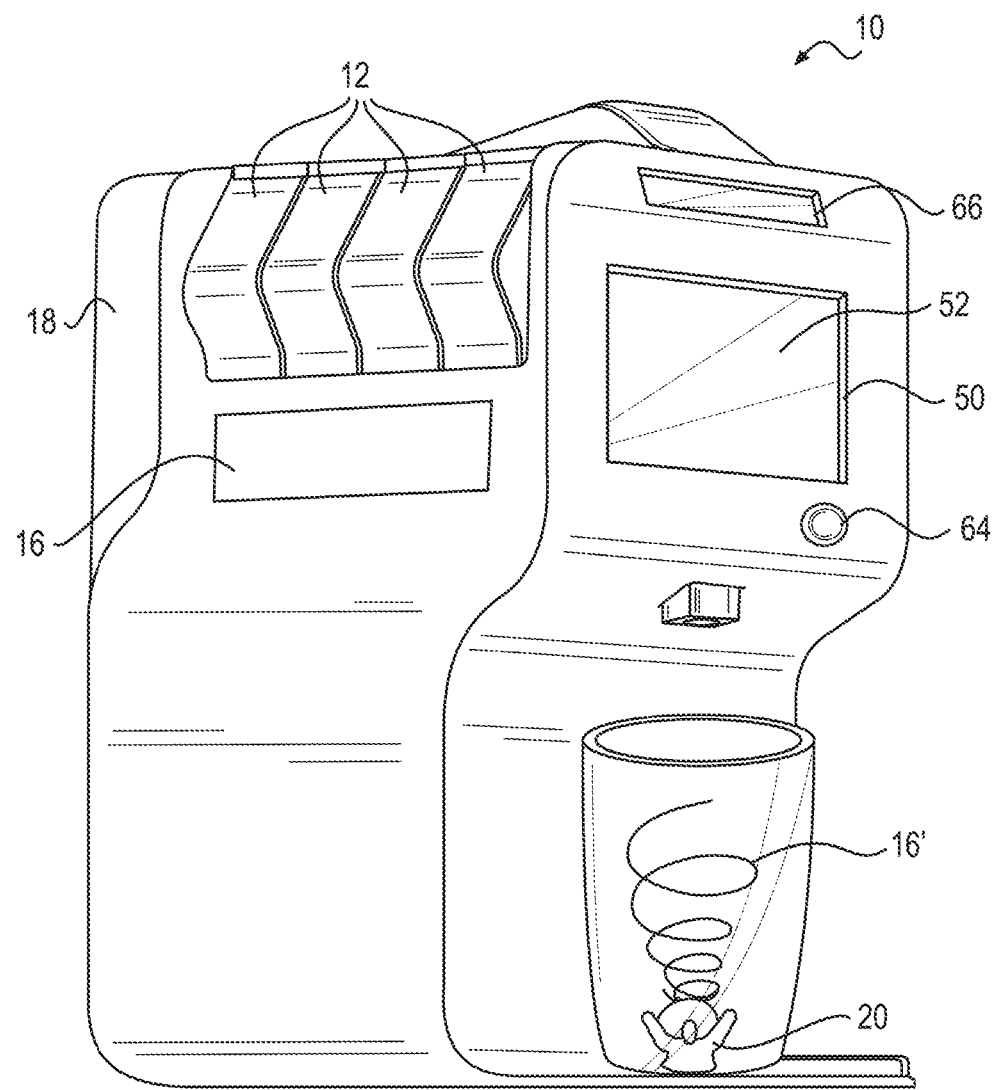
FIG. 2: is an illustration of an exemplary embodiment of a beverage delivery apparatus according to the present disclosure.

FIG. 2 shows the beverage delivery apparatus 10 according to an embodiment of the present disclosure. The beverage delivery apparatus 10 has a plurality of storage compartments 12. The storage compartments 12 may be located on both sides of the apparatus 10 and/or on a top portion of the apparatus 10 as illustrated in FIG. 1. It is preferred that the apparatus 10 has at least nine storage compartments 12.

Each of the storage compartments 12 configured to contain at least one canister 14 that contains the dietary and nutraceutical supplements.

In an embodiment of the present disclosure, the canister 14 has a unique identifier, for example, RFID strip or barcode) that can be read by sensors 11 (not shown) in the storage compartments 12 of the apparatus 10. When the canister 14 is inserted into the storage compartments 12 the sensor 11 reads the unique identification code on the identifier and then transmits the code to the data center 58. A software program application will then attempt to match the identification code with a container code registered in a code database of the data center 58. If there is no match, canister 14 is rejected. On the other hand, if the identification code matches the container the software program determines what type of nutrients are in the canister 14, and whether the contents of the canister 14 are safe to be consumed (e.g. whether the supplements contained in the canister 14 have been recalled, expired, or if the code was already registered/used). If the software program determines that the supplements do not meet all the preset requirements, the canister 14 will be rejected. If the software program determines that the supplements meet all the preset parameters, then the canister 14 will be registered to the user's specific apparatus and ready to be used.

The beverage delivery apparatus 10 further has a receiving chamber 16 that is configured to receive the dietary and nutraceutical supplements from the canister 14. The receiving chamber 16 allows for an access to a liquid that facilitates blending the dietary and nutraceutical supplements with the liquid to make a consumable beverage that contains the specific formulation of dietary and nutraceutical supplements supplied by the canisters 14.

In an embodiment of the present disclosure, the apparatus 10 further includes a container 18. The container 18 is configured to provide a liquid into the receiving chamber 16. In an alternative embodiment, the container 18 can be a standalone unit connected to the receiving chamber 16 by conventional means suitable for a delivery of liquid.

In another embodiment if the present disclosure, the receiving chamber can be a cup 16' that can be removed from the apparatus 10 and used for consuming the beverage. In this embodiment, the user may add the water or another liquid directly to the cup 16'. The cup 16' may also further contain a mixer-blender 20 to facilitate mixing of the supplements and liquid and to allow the addition of solid and semi solid product by the user.

Figure 3A:
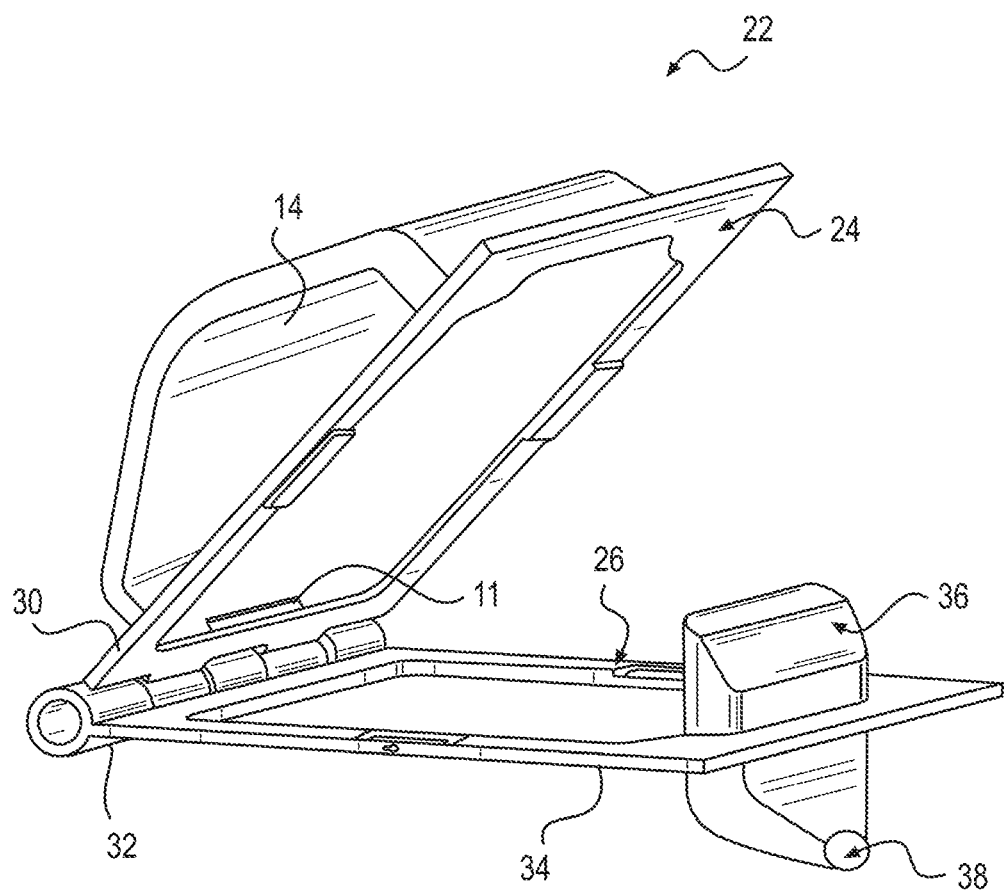
FIG. 3A: is a prospective view of an exemplary embodiment of a dispensing unit of the beverage delivery apparatus according to the present disclosure.
Figure 3B:
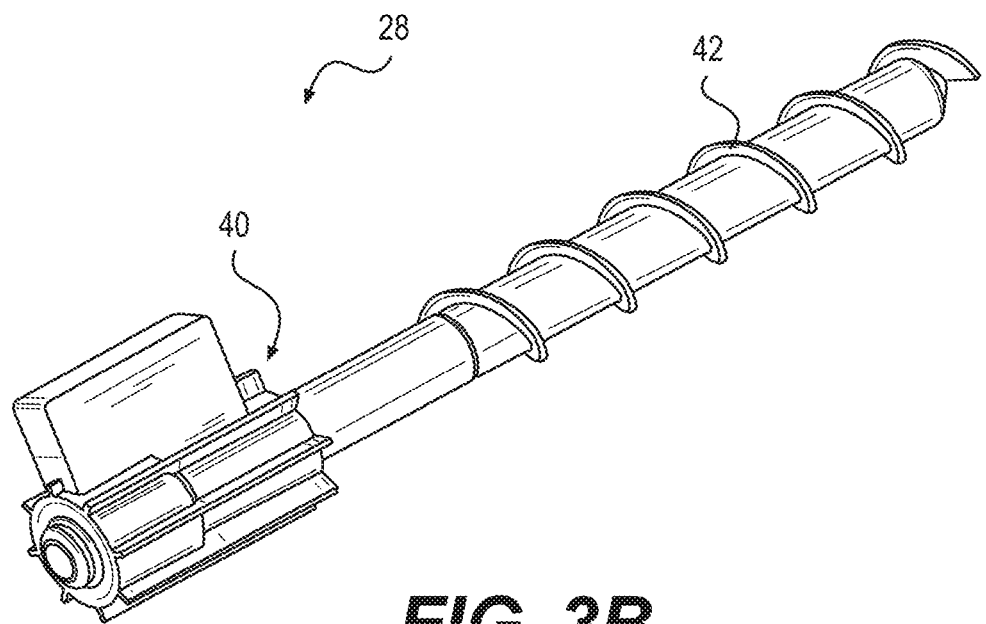
FIG. 3B: is a prospective view of an exemplary embodiment of a measuring assembly of the beverage delivery apparatus according to the present disclosure.
Figure 3C:
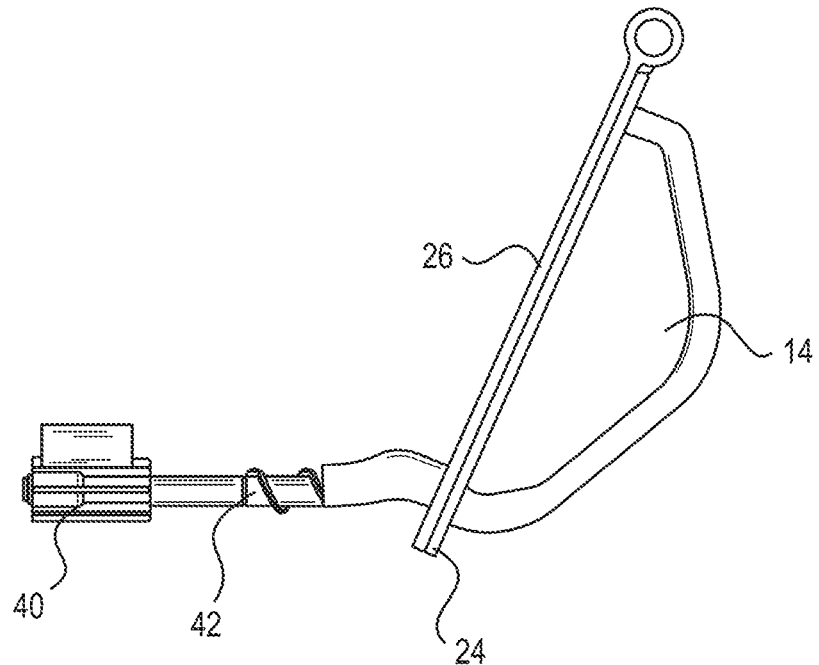
FIG. 3C: is a side view of an exemplary embodiment of the dispensing unit together with the measuring assembly of the beverage delivery apparatus according to the present disclosure.

In an embodiment of the present disclosure, the apparatus 10 further contains dispensing units 22 shown on FIGS. 3A-3C. Each storage compartment 12 has the dispensing unit 22. The dispensing unit is configured to dispense an amount of the supplements contained in the canister 14.

The dispensing unit has a top portion 24, a bottom portion 26 and a measuring assembly 28. The top portion 24 has a first end 30 and the bottom portion 26 has a hinge end 32 and a piercing end 34. The first end 30 of the top portion 24 connects the top portion 24 to the bottom portion 26 at the hinge end 32 of the bottom portion 26.

As shown on FIGS. 3A-3C, the top portion 24 is configured to receive the canister 14. The bottom portion 26 has a funneling part 36 configured to receive and dispense the dietary and nutraceutical supplements contained within the canister 14 when the top portion 24, having the canister 14 connected with the funneling part 36 of the bottom portion 26, and the dispensing unit 22 mechanically pivots to funnel the dietary and nutraceutical supplements into the receiving chamber 16. The measuring assembly 28 is connected to the dispensing unit 22 at an opening 38.

FIG. 3B shows the measuring assembly 28 according to an embodiment of this disclosure. The measuring assembly configured to measure by mass and volume the dietary and nutraceutical supplements contained in the canister 14.

According to an embodiment of the present disclosure, the measuring assembly 28 comprises a motor 40 and an auger screw 42. The motor 40 is configured to rotate the auger screw 42 thereby collecting predetermined of the supplements from the canister by the means of known number of turns that are needed in order to collect and dispense the exact amount of the supplements into the receiving chamber 16 or the cup 16'

In addition, the numbers of turns of the auger screw 42 are used to control the quantity of the supplements remaining in the canister after the predetermined amount of the supplement has been dispensed. Every canister is pre-registered to allow for only a certain amount of turns of the auger screw 42. After this number of turns is reached canister 14 would no longer be able to dispense the supplements. The user then will remove and replace the consumed canister 14.

It should be understood that other means of measuring the exact amounts of the supplements can be employed according to this disclosure. For example, volumetric dosage measuring devices can be employed, as well as the traditional and multi-head scales. Vibratory and various belt dosing may also be used.

Figure 4:
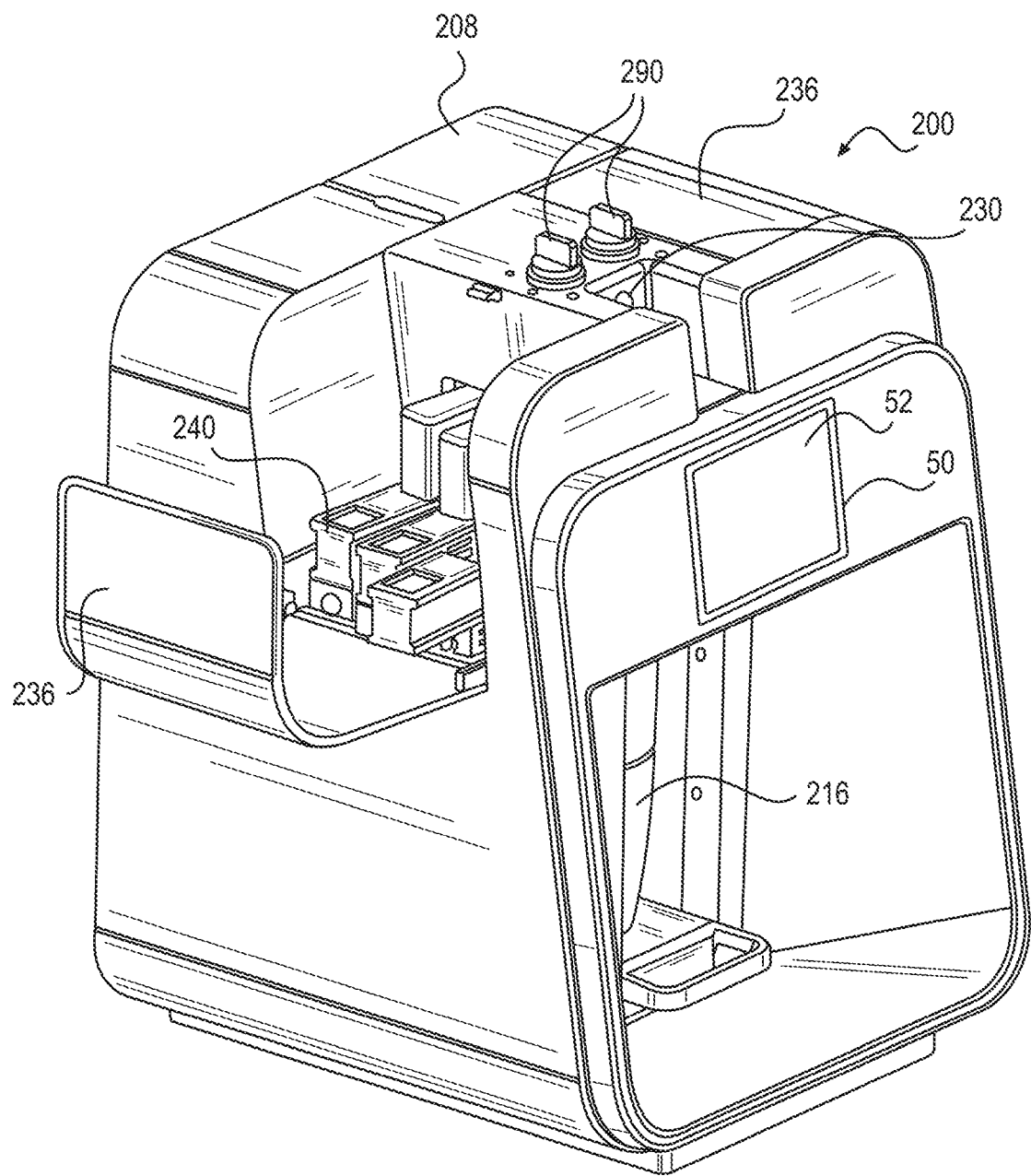
FIG. 4: is an illustration of a combination beverage delivery apparatus according to the present disclosure.

FIG. 4 illustrates another embodiment of the present disclosure, a combination beverage delivery apparatus 200. The combination beverage delivery apparatus 200 dispenses not only a beverage derived from a mixture of the dietary and nutraceutical supplements contained in multiple canisters, but also has a capability for a single-serve operation.

Figure 5B:
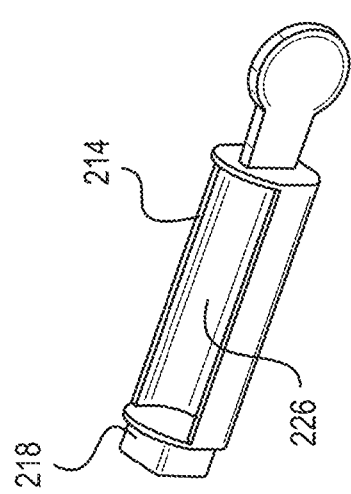
FIG. 5B: is a prospective view of an exemplary embodiment of the single-serve assembly of the combination beverage delivery apparatus according to the present disclosure.
Figure 5C:
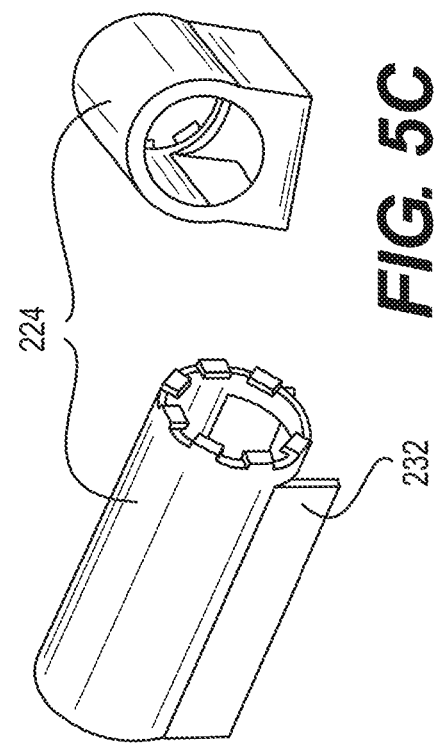
FIG. 5C: illustrates prospective views of the housing of an exemplary embodiment of the single-serve assembly of the combination beverage delivery apparatus according to the present disclosure.
Figure 5A:
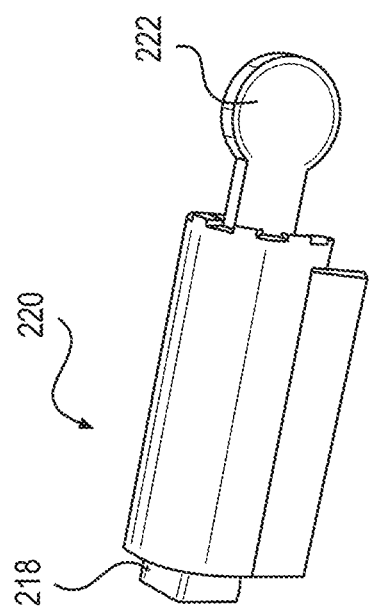
FIG. 5A: is a side view of an exemplary embodiment of a single-serve assembly of a combination beverage delivery apparatus according to the present disclosure.

FIGS. 5A to 5C illustrate a single-serve assembly 220. The single-serve assembly 220 comprises a cylindrical pod 214, shown on FIG. 5B, having a slot 226, a flange 218 and a turn handle 222. The flange 218 is configured to fit within a female opening of an insertion slot 230 of the apparatus 200. The cylindrical pod 214 contains a single serving of the dietary and nutraceutical supplements.

The cylindrical pod 214 is configured to fit within a single-serve housing 224. The single-serve housing 224 has a slit 232.

During the operation, the single-serve assembly 220 is placed into the insertion slot 230 and is securely fitted within the insertion slot 230 via connecting the flange 218 with its female counterpart (not shown) of the apparatus 200. The user by rotating the turn handle 222 180° aligns the slot 226 of the cylindrical pod 214 with the slit 232 of the single-serve housing 224, thereby dispensing the dietary and nutraceutical supplements contained in the pod 214 into the cup 216 via delivery channel (not shown).

Prior to the operation, the user must insert the single-serve assembly 220 into an insertion opening 230 of the combination beverage delivery apparatus 200. In the preferred embodiment the insertion opening 230 is located in front of the apparatus 230, above the cup 216 to allow for the direct ingress of the supplements into the cup 216. According to an embodiment of the present disclosure, the single-serve assembly 220 is provided to the user pre-assembled and containing the single serving of the dietary and nutraceutical supplements.

In addition, the combination beverage delivery apparatus 200 can be used to deliver a beverage that contains the dietary and nutraceutical supplements mixture that is derived from multiple of seeds and based on a recommendation of the nutrient recommendation engine 55.

FIG. 4 depicts a flap 236 in an open position exposing dispensing units 240 for delivering a mixture of the dietary and nutraceutical supplements. The number of the dispensing units 240 is, preferably, from two to nine. The dispensing units 240 can be placed on either or both sides of the combination beverage delivery apparatus 200 and are covered by the flap 236.

The apparatus 200 further may include a liquid container 208. The container 208 is configured to provide a liquid into a cup 216.

Figure 6:
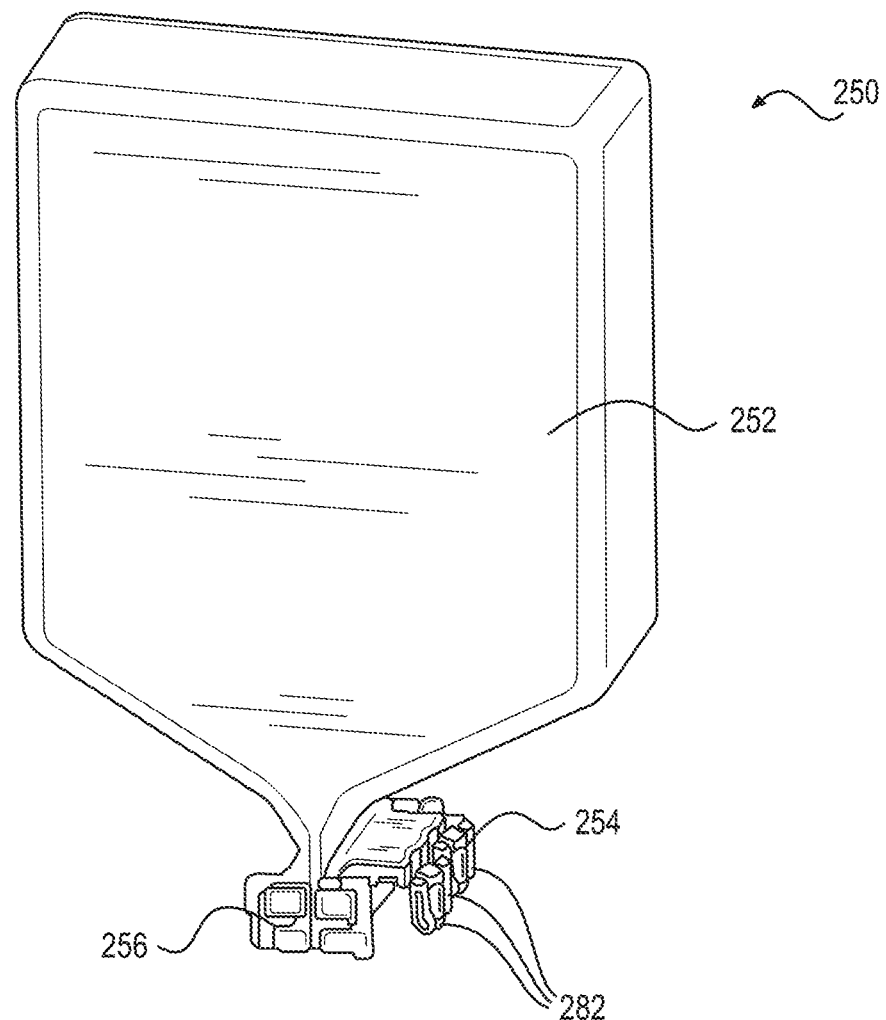
FIG. 6: is an illustration of a capsule assembly of the combination beverage delivery apparatus according to the present disclosure.

FIG. 6 illustrates a capsule assembly 250 for containing and delivery of a single-serve of the dietary and nutraceutical supplements. The capsule assembly 250 has a pouch 252 that holds the supplements, an identification technology 254 and a locking mechanism 256.

An embodiment according to the present disclosure of the dispensing unit 240 is shown on FIG. 7. The dispensing unit 240 comprises a drawer 258, a support 274, as well as a first guide 260 and a second guide 262 for receiving the identification technology 254 and the locking mechanism 256, respectively.

Figure 8:
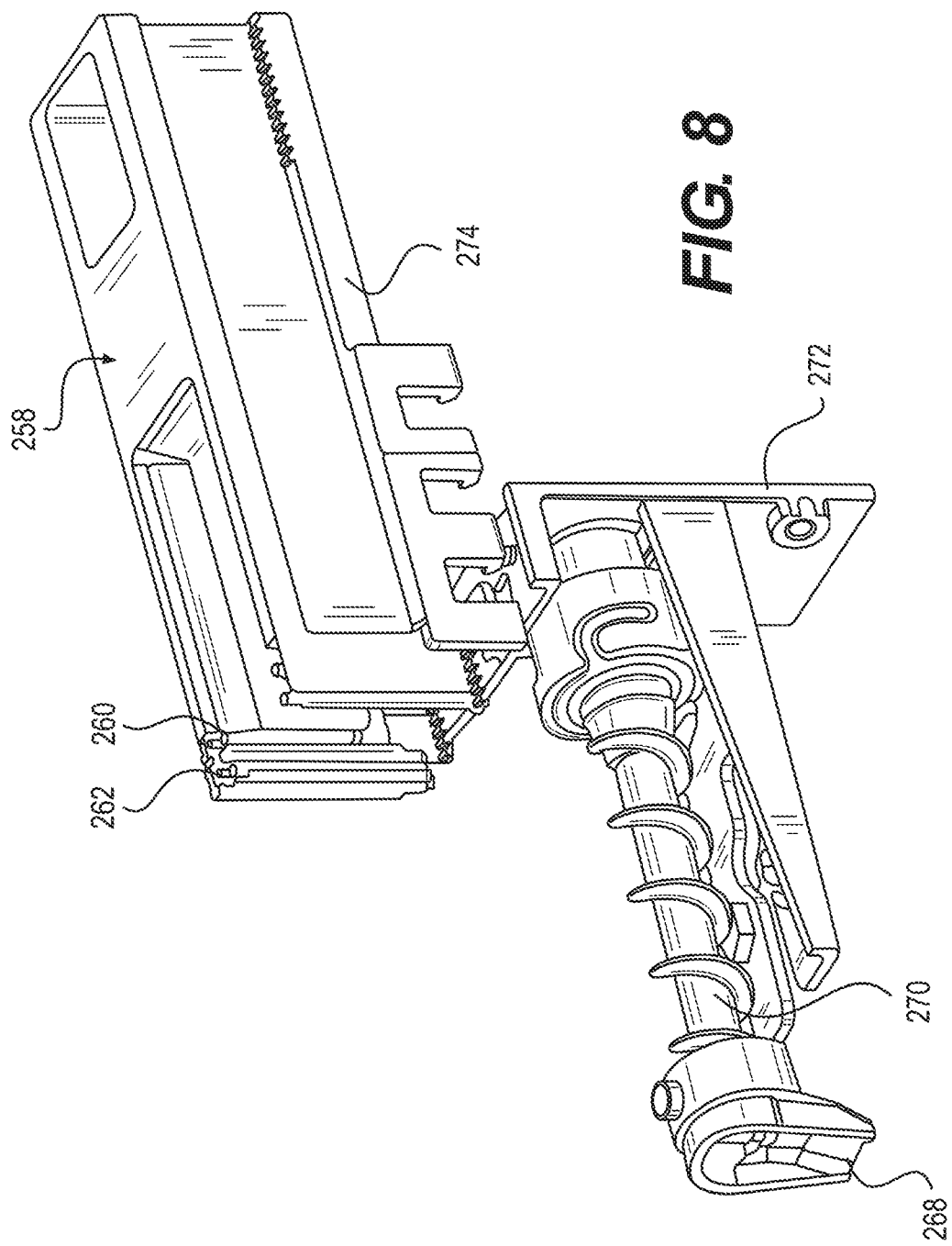
FIG. 8: is an illustration of an exemplary embodiment of a dosing screw of the combination beverage delivery apparatus according to the present disclosure.

Further, the dispensing unit 240 has a folding shutter 264, illustrated in the open position on FIG. 7, for preventing contamination of a dosing screw 270 shown on FIG. 8. The dosing screw 270 is enclosed within a canister 266 and terminates in a dispensing outlet 268 of the dispensing unit 240. The dispensing unit 240 can be mounted within the apparatus 200 via a bracket 272.

During the operation, the user inserts the capsule assembly 250 such way that the identification technology 254 is channeled through the first guide 260, and the locking mechanism 256 is guided through the second guide 262. The identification technology 254 is received by a detector 280 that is designed to recognize the content of the pouch 252 based on the number of teeth 282.

Once the capsule assembly 250 has been inserted as described in the preceding paragraphs, the user manually pushes the drawer 258 via railings 284. The identification technology 254 and the detector 280 are configured to remain locked during the close position of the drawer 258, while the locking mechanism 256 is configured to slide forward in the direction "A" illustrated by an arrow on FIG. 7 thereby opening the pouch and releasing its contents on the dosing screw 270.

The drawer 258 by being pushed forward in the direction "A" pushes the shutter 264 into close position to further illuminate any possibility of the contamination of the dosing screw 270. The shutter 264 has a spring 288 to allow the shutter 264 to move from open to close positions.

FIG. 4 and FIG. 9 illustrate the embodiment of the present disclosure that includes a flavoring component 290. FIG. 9 shows that the flavoring component 290 that is inserted into the combination beverage delivery apparatus 200. The flavoring component 290 comprises a flavor housing 290 and an exoskeleton 294, which is configured to receive a flavor pouch 296. The flavor pouch 296 contains a flavoring. The flavoring is preferably in a liquid form. The flavor pouch 296 further has a flavor outlet 298 with a counter pressure valve and a spring (not shown).

The flavor housing 292 also includes a pressure inlet 297 and a pressure control outlet 299 in order to increase and control pressure to bypass the counter pressure valve and release the predetermined volume of the flavoring to the cup 216.

Accordingly, when the user requires the apparatus 200 to deliver flavor to the dispensed beverage, the pressure is increased by a pressure pump through a pressure outlet thereby bypassing the counter pressure valve and releasing the flavoring to the cup 216. The pressure pump can be of any variety of mechanical pumps used for dispensing liquids.

The beverage delivery apparatuses described in this disclosure further may comprise a touch screen display 50. The touch screen display 50 serves as both an input device for the collection of data from the system user and the output device for displaying, for example, information relating to the user's health goal status or system status. Touch screen 50 displays a series of user interfaces (UI) 52 which serve to facilitate the collection and display of information between the user and the system 100.

The user data may be collected by various means. As illustrated on FIG. 1, the onboarding process can be initiated by the user through user interface 52 or remotely, for example, by means of a personal computer 63 or mobile devices 62 that are connected to the system 100 by, for example, WI-FI, Bluetooth or NFC/RFID. Each remote device may also include its own respective user interface that facilitates submission of the user data.

In order to further facilitate the exchange of information, as shown on FIG. 2, microphone 64 can be utilized to input verbal commands to system 100 and speakers 66 can be utilized to communicate choices and other information to the user. Verbal commands via microphone 66 would be translated using speech recognition software into instructions that could be interpreted by the nutrient recommendation engine 55. Additionally, the beverage delivery apparatus according the present disclosure may also contain a camera for further enhancing the exchange of information and the user experience.

According to an embodiment of the present disclosure the user is asked to go through an onboarding process where the user will provide the information, for example, regarding their name, age, gender, height, weight, and to fill out a health, wellness & goal assessment questionnaire.

The user may also submit a sample of their DNA (via saliva, stool, blood) for genome and microbiome sequencing through various providers, for example, Ubiome or Orig3n. The genome and microbiome sequencing is used to determine predispositions dictated by the users' genetic nutritional profile and microbiome characterization.

The user may also submit a blood and/or biological sample for diagnostic analysis through third party providers in order to receive more detailed information about the user's clinical chemistry, diseases, disease processes, and susceptibility.

The information provided by the above analysis may be submitted by the user through the touch screen display 50, user interface on the mobile device or supplied directly by the third-party analysis provider directly to the data center 58.

Yet another method of generating the user data can be bio-sensing wearable devices, for example, Apple® iWatch, Fitbit® or other similar devices that are capable of collecting the user's bio-data and transmitting the user data to the data center 58.

In an embodiment of the present disclosure, the user data can be also collected through non-wearable sensors outputs, for example digital weight and body fat percentage scales, digital glucose level measurement devices, and alike.

The user may also input nutrition information through, for example, user interfaces (UI) 52 of the apparatuses or the mobile device 62. The nutrition information may include, for example meals consumed or food calories intake. There are various mobile application that allow the user to determined the specific calories count in a food item. This nutrition information then submitted to the data center 58 in order to be analyzed by the nutrient recommendation engine 55 and integrated in its calculations, projections and/or recommendations.

The wearable devices may also aid in the input of the user data. For example, the wearable devices may provide food calories, macro and micronutrient "output," i.e. calories expanded during an exercise routine, the micronutrient lost via perspiration, the protein required for muscular construction.

Environmental data (pollution, humidity, level of pollen, bio hazards, and the like) could also be used as part of the user data. For instance, the high level of pollution in the air could increase the content of anti-oxidants inside the drink that specific day to counter effect the environmental condition.

The nutrient recommendation engine 55 analyzes these information inputs to recommend a range of vitamins, minerals, macronutrients, pro and prebiotics, herbs and specialty nutrients, for example, Omega-3 for the user to consume in order for the user to achieve the present health, fitness and other personal goals.

Figure 10:
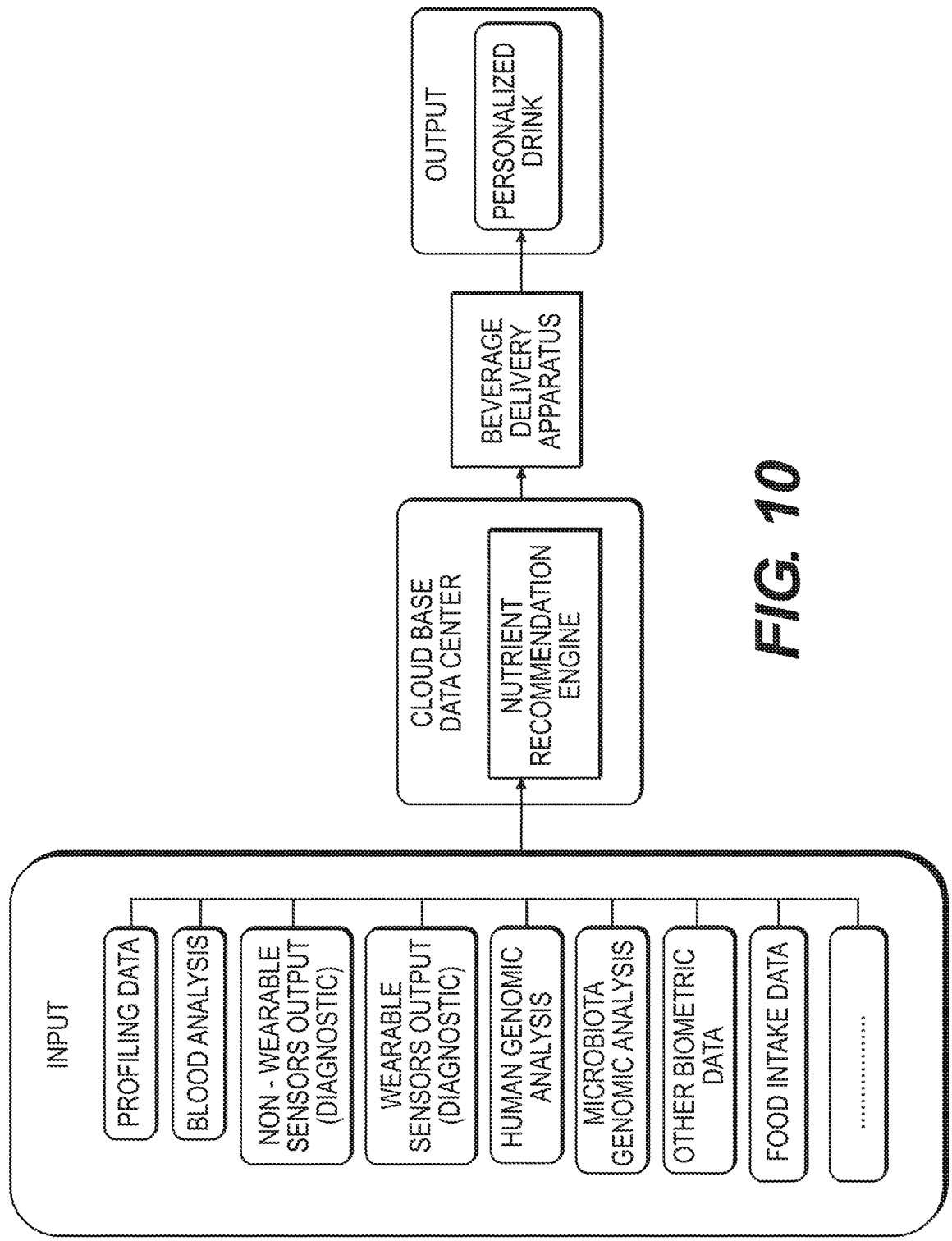
FIG. 10: depicts a flowchart of a method of delivering a customized dietary and nutraceutical supplements to a user according to the present disclosure.

FIG. 10 illustrates an embodiment of the present disclosure, where the system 100 delivers to the user the customized beverage. The nutrient recommendation engine 55 is configured to provide the user a personalized action plan (e.g. a combination of a diet regimen, nutrition regimen, supplements/vitamins, and physical fitness). The personalized action plan may also include a schedule and the nutrition regimen, e.g., of when to take the specific nutrients, what combination, and in what quantity. There is also may be a fitness regimen, based on the user's genome report and other user data.

In an embodiment of the present disclosure, the nutrient recommendation engine 55 is configured to analyze the user's longitudinal and historical data, from for example, diagnostic testing and EHR/EMRs, through predictive analytics models to identify behavioral and physiological patterns and to measure resulting outcomes. The predictive analytics model uses identified patterns to forecast the positive and/or negative trajectory of a pattern and predict how the pattern will impact the user's wellness, typically over longer periods of time (months to years). The nutrient recommendation engine 55 improves the confidence of forecasts generated by the model over time by employing a closed feedback loop to measure the accuracy of previous predictions based on the data that was available at the time of the forecast against the data that was collected during the forecast.

The nutrient recommendation engine 55 learning techniques are employed by the nutrient recommendation engine 55 to predict certain health outcomes for supplements' recommendations from data with significantly smaller sample size of historical data. The nutrient recommendation engine 55 absorbs real-time, high resolution user generated data, for example, from bio-sensing wearables to analyze the difference between the intended impacts of a nutritional recommendation on the user's health and the real-world measurements and outcomes. The nutrient recommendation engine 55 determines the degree of accuracy of the recommendation and measures its effectiveness over time to validate or modify the calculations behind the recommendation.

As discussed in this disclosure, the user data captured through various data sources such as bio-sensing wearables, EHR/EMRs, clinical records, health/fitness/wellness applications, health data aggregators/repositories/device data stores (such as Google Fit, Apple Health, Samsung S Health, Microsoft Health) that are connected to the data center 58 are aggregated by the nutrient recommendation engine 55. The resolution of this data can range from historical to real-time intervals. When new data is received from the data sources described in this disclosure or later developed, the nutrient recommendation engine 55 generates a record of the previous values and updates the user's data profile with the most recent values and measurements. The engine 55 utilizes updated data values and measurements to automatically and in real-time adjust the user's nutrient consumption and recommendations by, for example, increasing or decreasing the quantities of nutrients and dietary supplements, adding or removing nutrients, or altering the timing of consumption.

The capacity of the system 100 to adapt immediately to changes, allows creating a unique health signature.

For the nutrition regimen, the user may be provided with customized dietary and nutraceutical supplements through the system 100 multiple times throughout the day, preferably when the user wakes up, after each meal, before, during, and after fitness exercise, and before sleep.

In an embodiment of the present disclosure, in order to calculate the precise quantity of nutrients the user's body requires to achieve the user's goals (e.g. preset parameters), the nutrient recommendation engine 55 utilizes the Nutrient Balance Concept (NBC).

The NBC was developed using the USDA Food Composition Database (Release 27) and illustrated with the MyPlate 7-day sample menus for a 2000 calorie food pattern. The NBC concept is centered on three specific metrics for a given food, meal or diet—a Qualifying Index (QI), a Disqualifying Index (DI) and a Nutrient Balance (NB). The QI and DI were determined, respectively, from the content of 27 essential nutrients and 6 nutrients associated with negative health outcomes. The third metric, the Nutrient Balance (NB), was derived from the Qualifying Index (QI) and provided key information on the relative content of qualifying nutrients in the food. Because the Qualifying and Disqualifying Indices (QI and DI) were standardized to energy content, both become constants for a given food/meal/diet and a particular consumer age group, making it possible to develop algorithms for predicting nutrition quality when combining different foods. Combining different foods into composite meals and daily diets led to improved nutrition quality as seen by QI values closer to unity (indicating nutrient density was better equilibrated with energy density), DI values below 1.0 (denoting an acceptable level of consumption of disqualifying nutrients) and increased NB values (signifying complementarity of foods and better provision of qualifying nutrients).

In an embodiment of the present disclosure, a modified NBC approach, Mixfit Balance Concept (MBC) is used in order to calculate the precise quantity of nutrients the user's body requires to achieve his or her goals. NBC score is modified by integrating specific energy (Kcal) and nutrients (mg) derived from onboarding process or other means from the user.

According to this embodiment, i.e. MBC, the following formulas are used in order to calculate the qualifying index (QI) and disqualifying index (DI):

$$QI = \frac{E_d}{E_p} \cdot \frac{\sum_{j=1}^{N_q} \frac{a_{q,j}}{r_{q,j}}}{N_q}$$

$$DI = \frac{E_d}{E_p} \cdot \frac{\sum_{j=1}^{N_d} \frac{a_{d,j}}{r_{d,j}}}{N_d}$$

wherein
Ed: daily energy needs of the specific user for the specific day
Ep: Energy in the amount of the meal analyzed
Aq,j: amount of qualifying nutrients in the food analyzed (mg/day)
Ad,j; amount of disqualifying nutrients in the food analyzed (mg/day)
R q,j: Adaptive DRI of qualifying nutrients (mg/day)
R d,j: MRV of disqualifying nutrients (mg/day)
Nq: Number of qualifying nutrients considered
Nd: number of disqualifying nutrients considered.

In addition, the Dietary Reference Intakes (DRIs), estimated average requirements published by Food and Nutrition Board, Institute of Medicine, National Academics may be used in order to determine the required daily intake of every user and adjust the NBC as further described below. The DRIs are measured in milligrams (mg). The upper limits (UL) of DRIs function as limitations and never surpassed. When supplements are provided in combination (mixed beverage) it is important to have a range of tolerance which is defined between DRI and UL.

For example, the basic DRI for a single user can be adjusted as follows:
Physical activities would ADD nutrients requirements
Physical conditions would MODIFY nutrients requirements
Allergies would MODIFY nutrients requirements
Diets (e.g., vegan-paleo-etc.) would ADD nutrients requirements With respect to energy represented in kilocalories (Kcal), the Basic Metabolic Rate (BMR) is used to calculate the precise quantity of nutrients the user's body requires to achieve his or her goals and adjust the NBC as further described below. The Mifflin-St Jeor formula published by American Dietetic Association (ADA) can be chosen to calculate BMR of the user. The formula for men and women is presented below:

Men

10×weight (kg)+6.25×height (cm)−5×age($y$)+5

Women

10×weight (kg)+6.25×height (cm)−5×age($y$)−161

If the user does not use the activity tracker, such as Fitbit® or iWatch®, the level of activities can be established by a preset value. For example, based on the user's onboarding questioner, the following can be used as the determination of level of activity.

| Activity Type | LAF |
|---|---|
| Sedentary | 1.2 |
| Light | 1.375 |
| Moderate | 1.55 |
| Active | 1.725 |
| Very Active | 1.9 |

The daily calorific need (DCN) is then calculated as follows:

DCN=BMR×LAF

Once the DCN (Kcal) is calculated a desired amount of nutrients (proteins, fats, and the like) can be obtained based on the user's preset goals. The DCN calculated in Kcal can then be converted into grams.

Accordingly, when the user employs wearable devices, LAF can be automatically calculated. When wearable devices are used LAF is usually between 1 and 2. This allows calculate the correct amount of calories needed to achieve user's goals (personalized caloric intake) in real time.

It is understood that the present invention is not limited to utilizing the NBC or modified NBC, MBC, described in the previous paragraphs. It is further understood that the nutrient recommendation engine 55 may utilize various concepts, methods and/or algorithms, alone or in combination in order to calculate the precise quantity and/or volume of supplements the user requires to achieve his or her goals. Other known methods are: DRI (daily required Intake), NRV (nutrient reference value) or any other publicly disclosed or of privately owned method.

After a period of time the user may submit the blood sample for analysis to verify if the supplements are having their intended effects and the user is achieving the intended results. The blood analysis shows the current level of nutrient needs of user's body.

Also, preferably, the blood analysis and microbiome sequence should be performed regularly, and preferably, in six months intervals in order to verify that the supplements recommendations by the nutrient recommendation engine 55 are having the intended effects.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A dispensing system for delivering a beverage with customized quantities of dietary and nutraceutical supplements and flavor in single and/or multi-serve configurations, the dispensing system comprising:
- a beverage delivery apparatus having a plurality of storage compartments each configured to store at least one canister, wherein each canister contains dietary and nutraceutical supplements, and wherein each of the storage compartments further comprising:
- a dispensing unit having a top portion, a bottom portion and a measuring assembly, wherein the top portion has a first end and the bottom portion has a hinge end and a piercing end, and the first end of the top portion connects the top portion to the bottom portion at the hinge end of the bottom portion, and wherein the top portion is configured to receive the canister and the bottom portion has a funneling part configured to receive and dispense the dietary and nutraceutical supplements contained within the canister when the top portion having the canister connected with the funneling part of the bottom portion and the dispensing unit pivots to dispense the dietary and nutraceutical supplements contained within the canister, and wherein the measuring assembly comprises a motor and an auger screw, wherein motor is configured to rotate the auger screw thereby collecting predetermined quantiles of the dietary and nutraceutical supplements by the means of a known number of turns that are needed in order to collect and dispense an exact amount of the dietary and nutraceutical supplements;
- a receiving chamber configured to receive the dietary and nutraceutical supplements from the dispensing unit and to blend the dietary and nutraceutical supplements with a liquid;
- a single-serve assembly configured to dispense a single serving of the dietary and nutraceutical supplements into the beverage;
- at least one flavoring component configured to deliver a flavored ingredient to the beverage;
- a liquid container;
- a controller for controlling dispensing of the customized quantities of dietary and nutraceutical supplements;
- a cloud-base data center that comprises a nutrient recommendation engine which is configured to collect and analyze a user data, categorize the user data and to communicate with the dispensing unit through the controller a type and a dosage of the dietary and nutraceutical supplement to be dispensed into the receiving chamber based on the user data.

2. The dispensing system according to claim 1, further comprising at least one mobile device connected with the cloud-base data center and configured to communicate the user data to the cloud-base data center.

3. The dispensing system according to claim 1, further comprising at least one monitoring device connected with the cloud-base data center and configured to communicate the user data to the cloud-base data center in real time.

4. The dispensing system according to claim 3, wherein the at least one monitoring device is capable of collecting the user's bio-data in real time, wherein the user's bio-data comprises bioenergy and nutrients consumption, bioenergy and nutrients intake, heart rate and/or physical activity.

5. The dispensing system according to claim 1, wherein the user data comprises information on biometrics data, direct and indirect input on food consumption, nutritional goals and activities.

6. The dispensing system according to claim 1, wherein the nutrient recommendation engine configured to create a personalized nutrient mix regimen profile and to provide specific recommendation of a mix of the dietary and nutraceutical supplements based on the personalized nutrient mix regimen profile of the user and the user data.

7. The dispensing system according to claim 1, further comprising a user identification component.

8. The dispensing system according to claim 1, wherein the beverage delivery apparatus further comprises a user interface configured to allow the user to input the user data and/or approve a delivery of a consumable beverage by the dispensing system.

9. The dispensing system of claim 1, wherein the nutrient recommendation engine uses a modified Nutrient Balance Concept (NBC) having a qualifying index (QI) and a disqualifying index (DI) calculated by formula (I) and formula (II):

$$QI = \frac{E_d}{E_p} \cdot \frac{\sum_{j=1}^{N_q} \frac{a_{q,j}}{r_{q,j}}}{N_q} \quad (I)$$

$$DI = \frac{E_d}{E_p} \cdot \frac{\sum_{j=1}^{N_d} \frac{a_{d,j}}{r_{d,j}}}{N_d} \quad (II)$$

wherein
- $E_d$: daily energy needs of the specific user for the specific day
- $E_p$: Energy in the amount of the meal analyzed
- $A_{q,j}$: amount of qualifying nutrients in the food analyzed (mg/day)
- $A_{d,j}$: amount of disqualifying nutrients in the food analyzed (mg/day)
- $R_{q,j}$: Adaptive DRI of qualifying nutrients (mg/day)
- $R_{d,j}$: MRV of disqualifying nutrients (mg/day)
- $N_q$: Number of qualifying nutrients considered
- $N_d$: number of disqualifying nutrients considered.

10. The dispensing system of claim 1, wherein the flavoring component comprises
- a flavor housing;
- an exoskeleton, the exoskeleton is configured to receive a flavor pouch, wherein the flavor housing has a pressure inlet and a pressure control outlet configured to increase and control pressure to bypass a counter pressure valve of the flavor pouch and release the predetermined volume of a flavoring.

11. The dispensing system of claim 1, wherein each dispensing unit of the plurality of dispensing units further comprises:
- a drawer slidably connected to a support;
- a first guide and a second guide configured to receive an identification technology and a locking mechanism of the capsule assembly, respectively, and the identification technology formed to be received by a detector;
- a dosing screw that terminates in a dispensing outlet; and
- a bracket configured to fixedly attach the dispensing unit to the apparatus.

* * * * *